US010542963B2

(12) United States Patent
Kim et al.

(10) Patent No.: US 10,542,963 B2
(45) Date of Patent: Jan. 28, 2020

(54) ULTRASOUND PHANTOM FOR FOCUSED ULTRASOUND, METHOD FOR MANUFACTURING THE SAME, BIOMIMETIC HYDROGEL PHANTOM, METHOD FOR MANUFACTURING THE SAME, DISCOLORING METHOD AND DRUG DELIVERING METHOD USING THE SAME

(71) Applicant: KOREA RESEARCH INSTITUTE OF STANDARDS AND SCIENCE, Daejeon (KR)

(72) Inventors: Se Hwa Kim, Daejeon (KR); Yong Tae Kim, Daejeon (KR); Dong Hee Ma, Daejeon (KR)

(73) Assignee: Korea Research Institute of Standards and Science (KR)

( * ) Notice: Subject to any disclaimer, the term of this patent is extended or adjusted under 35 U.S.C. 154(b) by 468 days.

(21) Appl. No.: 15/243,254

(22) Filed: Aug. 22, 2016

(65) Prior Publication Data
US 2017/0333007 A1    Nov. 23, 2017

(30) Foreign Application Priority Data

May 17, 2016 (KR) .......................... 10-2016-0060110

(51) Int. Cl.
*A61B 8/00* (2006.01)
*A61K 49/22* (2006.01)
(Continued)

(52) U.S. Cl.
CPC .............. *A61B 8/587* (2013.01); *A61K 49/22* (2013.01); *B29B 7/08* (2013.01); *B29C 39/003* (2013.01);
(Continued)

(58) Field of Classification Search
CPC ....... A61B 8/587; B29C 39/003; B29C 39/02; A61K 49/22; B29B 7/08; B29K 2105/0061; B29K 2005/00; B29K 2105/0064; B29K 2995/0001; B29K 2105/0035; B29L 2031/40; B29L 2031/753
See application file for complete search history.

(56) References Cited

FOREIGN PATENT DOCUMENTS

KR   2008-0080510 A   9/2008
KR      1134051      4/2012
(Continued)

OTHER PUBLICATIONS

"Acoustic Characteristics of a Tissue Mimicking Phantom for Visualization of Thermal Distribution", Kim et al., see attached publication. (Year: 2012).*
(Continued)

*Primary Examiner* — Xin Y Zhong
(74) *Attorney, Agent, or Firm* — Akerman LLP

(57) ABSTRACT

The present disclosure relates to an ultrasound phantom for a focused ultrasound wave. More specifically, the present invention provides an ultrasound phantom which mimics a body so as to correspond to a speed of sound in the body, in which agarose, sucrose, polydiacetylene vesicle, and distilled water are mixed, and a specific part onto which an ultrasound wave is irradiated by a focused ultrasound transducer is gradually discolored in accordance with a temperature.

3 Claims, 13 Drawing Sheets

(51) Int. Cl.
   *B29B 7/08* (2006.01)
   *B29C 39/00* (2006.01)
   *B29C 39/02* (2006.01)
   *B29K 105/00* (2006.01)
   *B29L 31/40* (2006.01)
   *B29L 31/00* (2006.01)

(52) U.S. Cl.
   CPC .......... *B29C 39/02* (2013.01); *B29K 2005/00* (2013.01); *B29K 2105/0035* (2013.01); *B29K 2105/0061* (2013.01); *B29K 2105/0064* (2013.01); *B29K 2995/0001* (2013.01); *B29L 2031/40* (2013.01); *B29L 2031/753* (2013.01)

(56) References Cited

FOREIGN PATENT DOCUMENTS

| | | |
|---|---|---|
| KR | 2014-0001037 A | 1/2014 |
| KR | 2014-0113173 A | 9/2014 |
| WO | 2009/103220 A1 | 8/2009 |

OTHER PUBLICATIONS

"Time-temperature chromatic sensor based on polydiacetylene vesicle and amphiphilic copolymer", Gou et al., see attached publication. (Year: 2010).*

* cited by examiner

[FIG. 1]
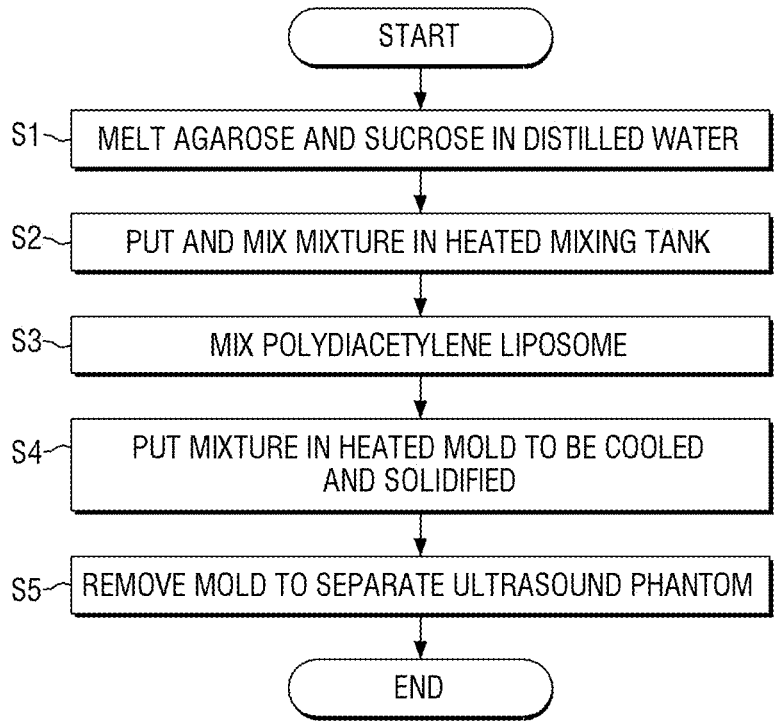
[FIG. 2]
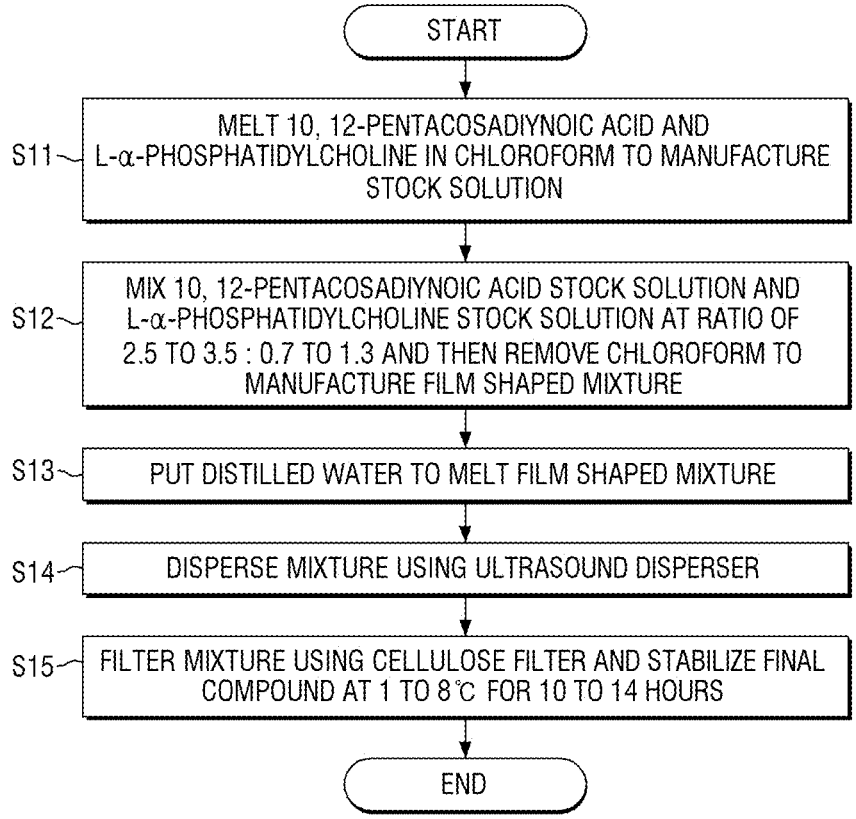

[FIG. 3]
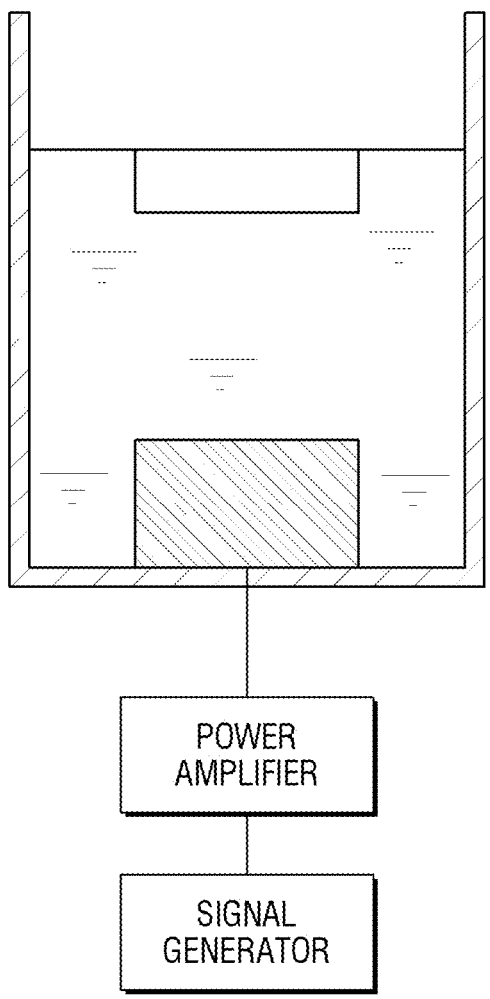

[FIG. 4]
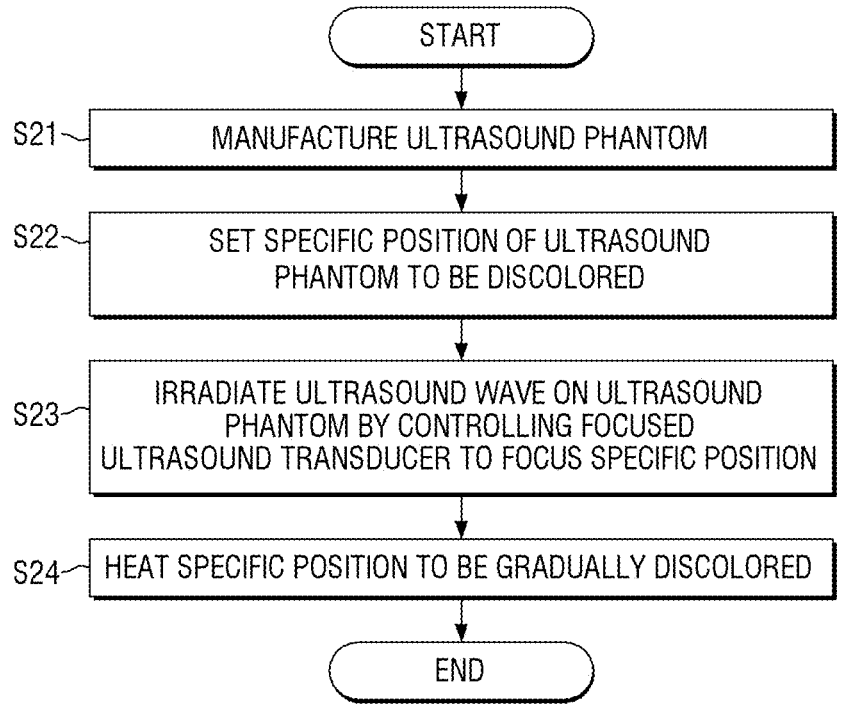
[FIG. 5]
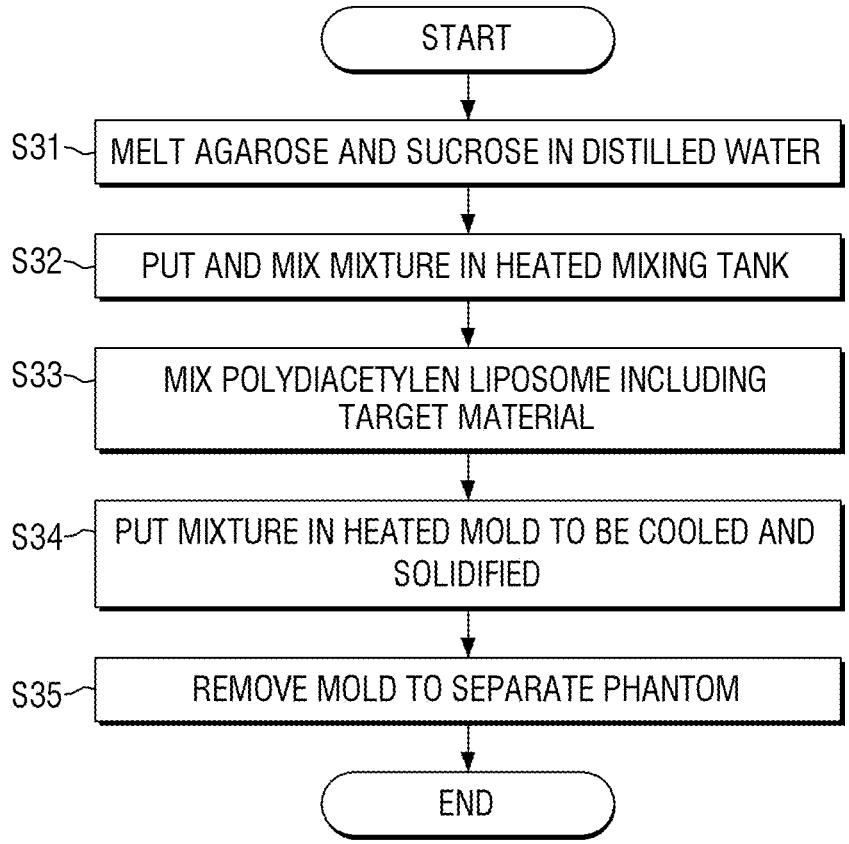

[FIG. 6]
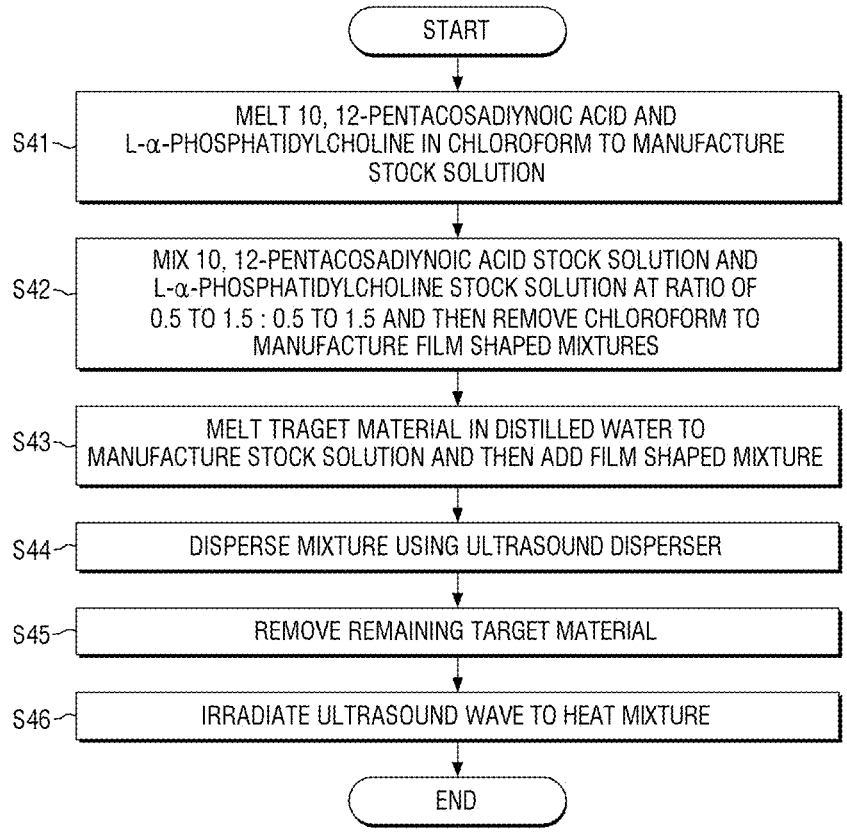
[FIG. 7]
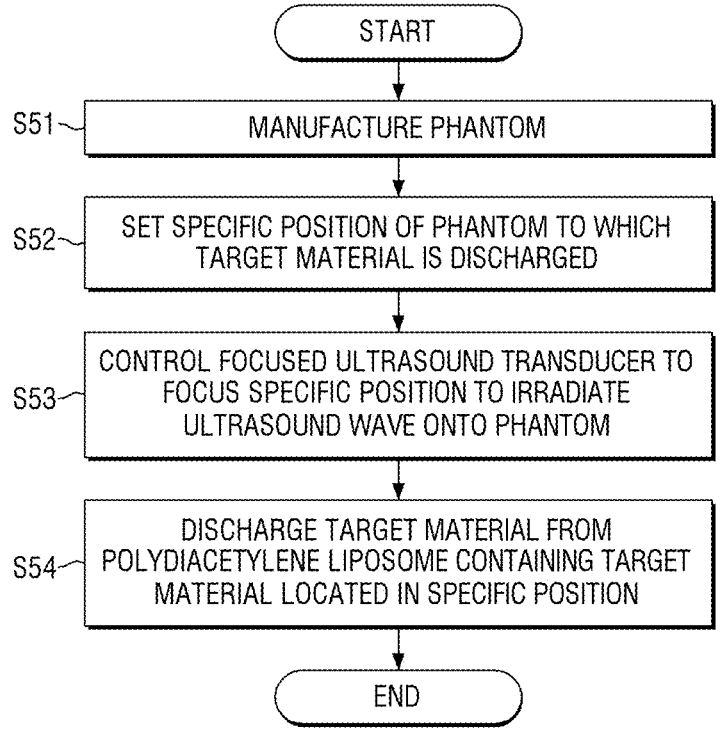

[FIG. 8A]
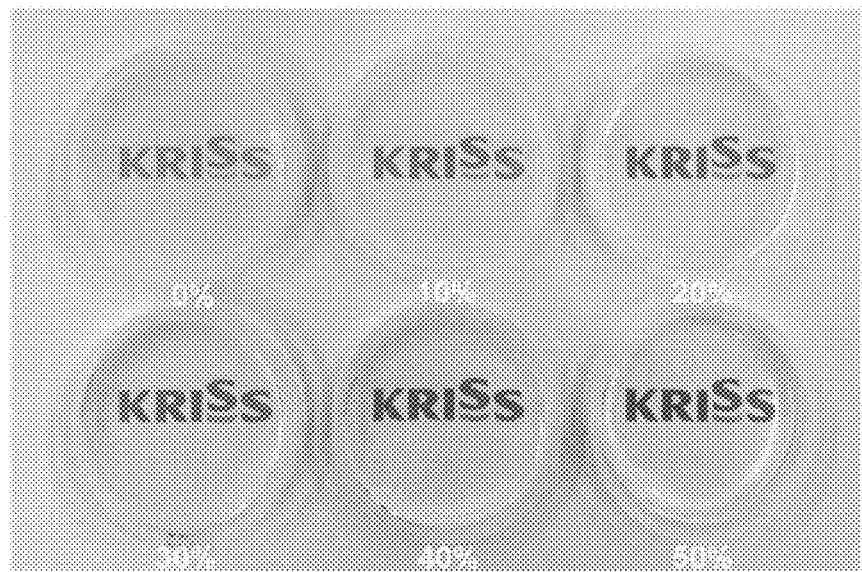
[FIG. 8B]
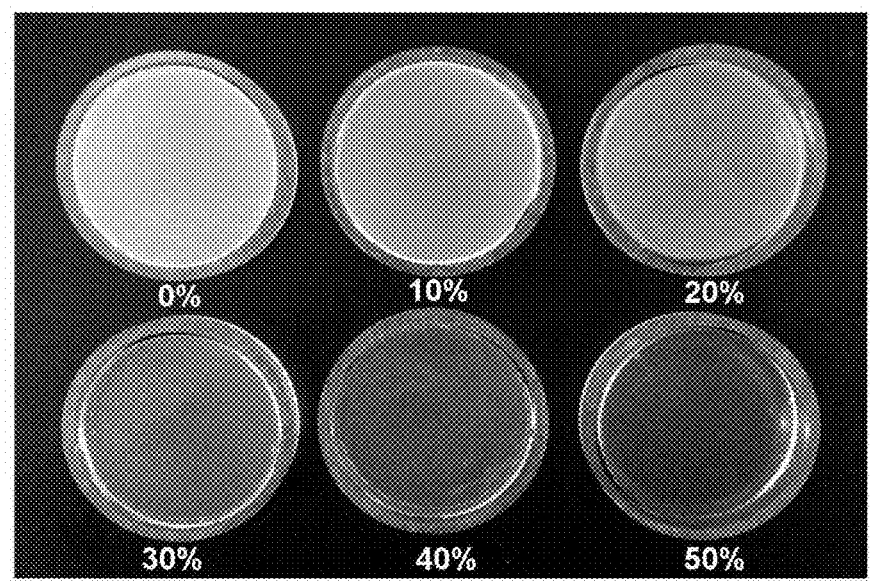

[FIG. 9]
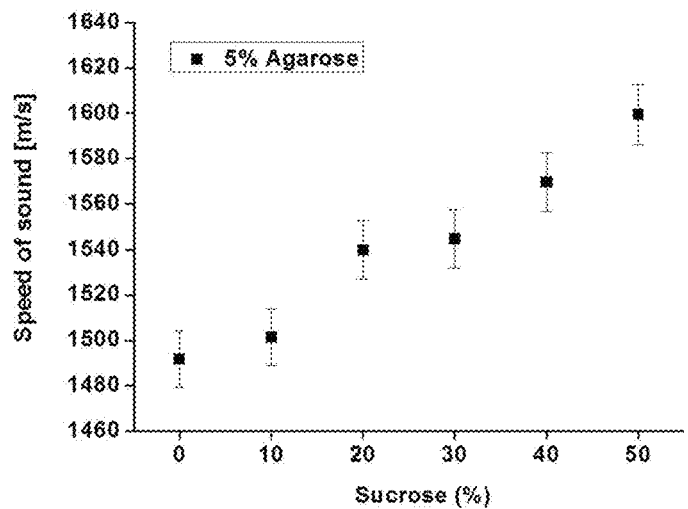
[FIG. 10A]
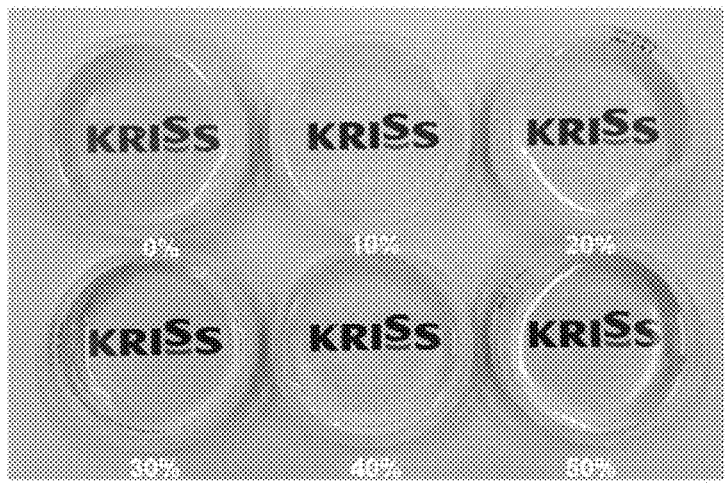
[FIG. 10B]
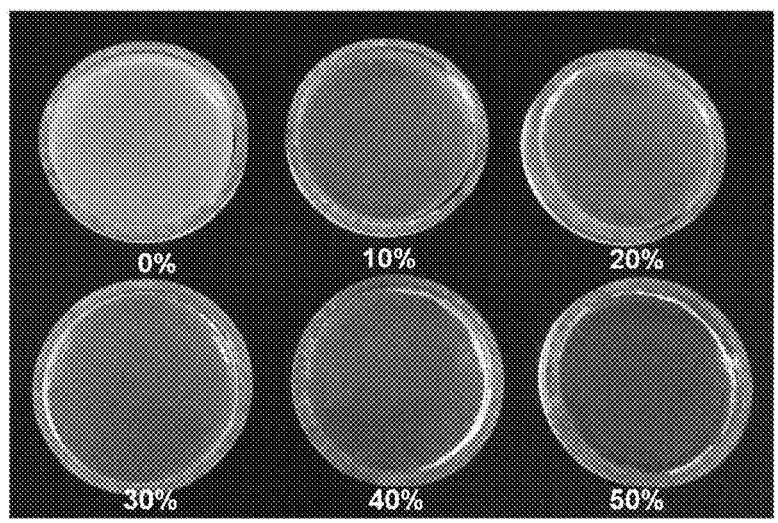

[FIG. 11]
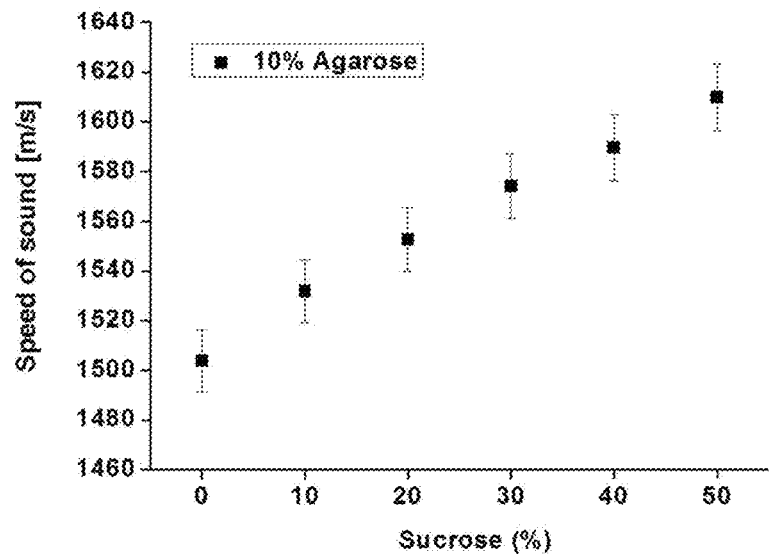
[FIG. 12]
| Agarose (%) | Sucrose (%) | v_ps (m/s) |
|---|---|---|
| 5 | 0 | 1491.8 |
|   | 10 | 1501.4 |
|   | 20 | 1539.8 |
|   | 30 | 1544.6 |
|   | 40 | 1569.6 |
|   | 50 | 1599.3 |
| 10 | 0 | 1503.8 |
|   | 10 | 1531.8 |
|   | 20 | 1552.6 |
|   | 30 | 1574.2 |
|   | 40 | 1589.6 |
|   | 50 | 1609.7 |

[FIG. 13]
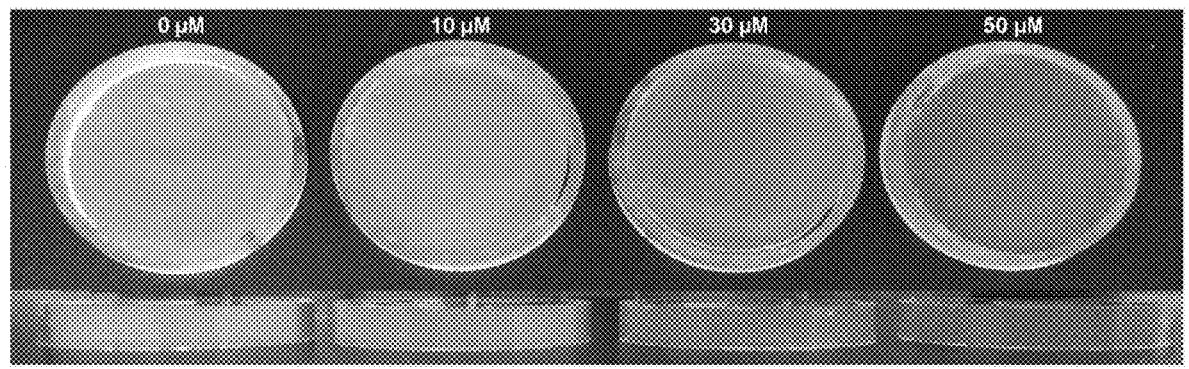
[FIG. 14]
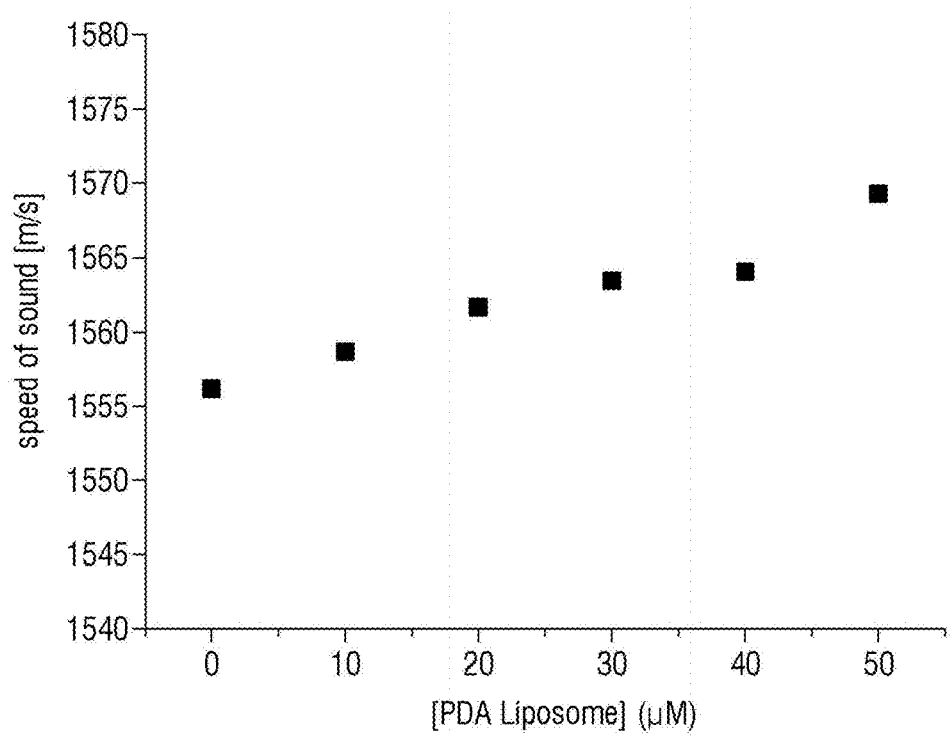

[FIG. 15]
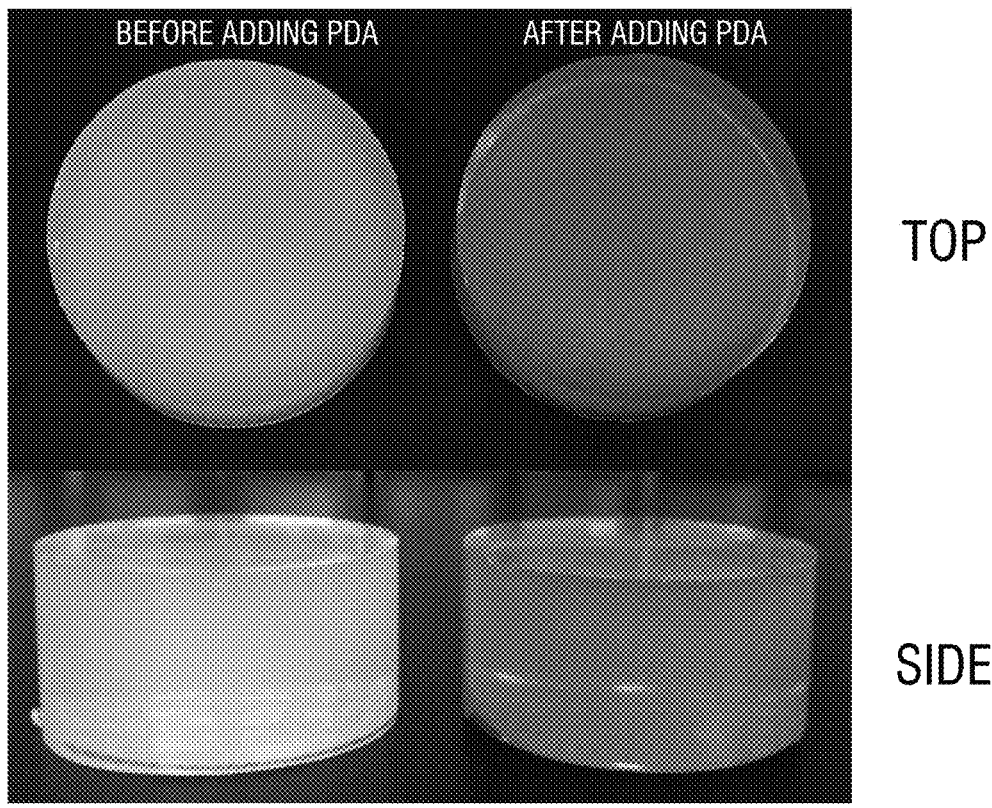
[FIG. 16A]
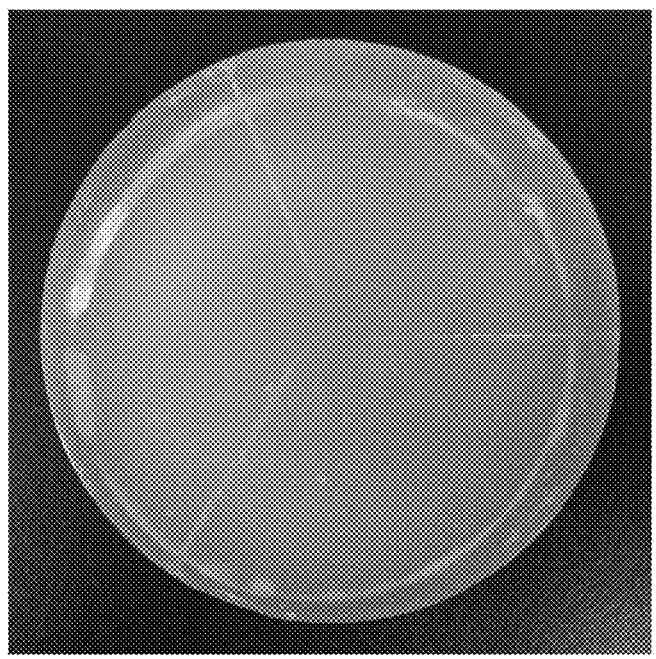

[FIG. 16B]
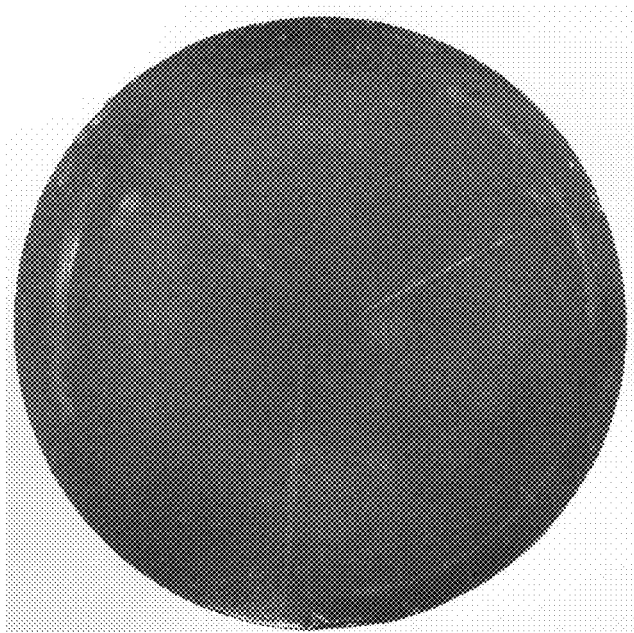
[FIG. 17]
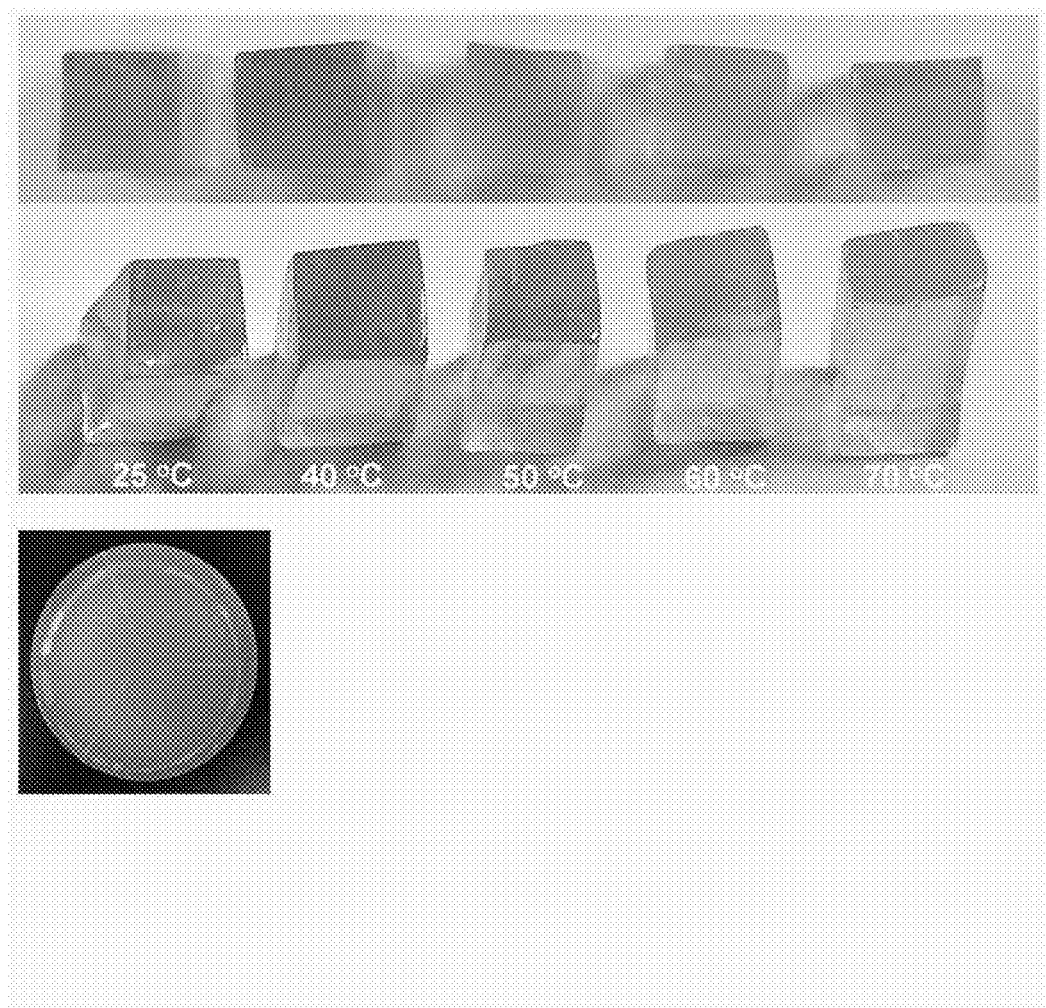

[FIG. 18]
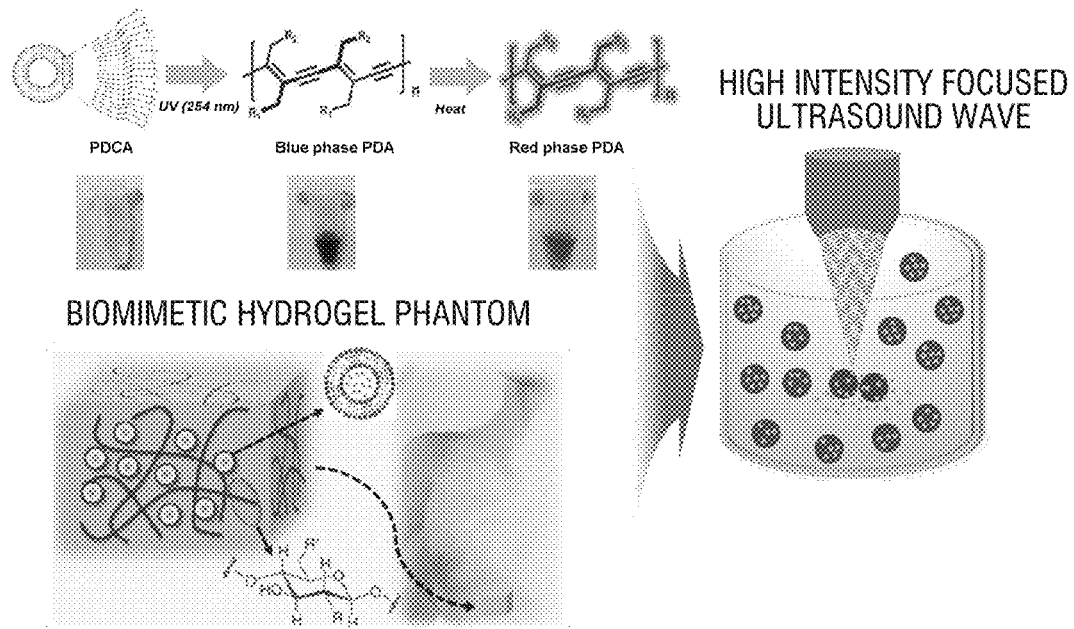

[FIG. 19]
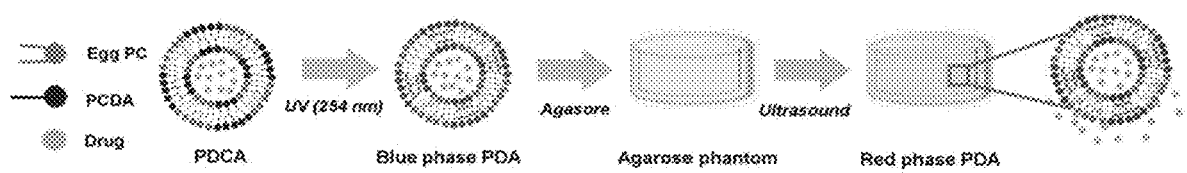

[Fig. 20]
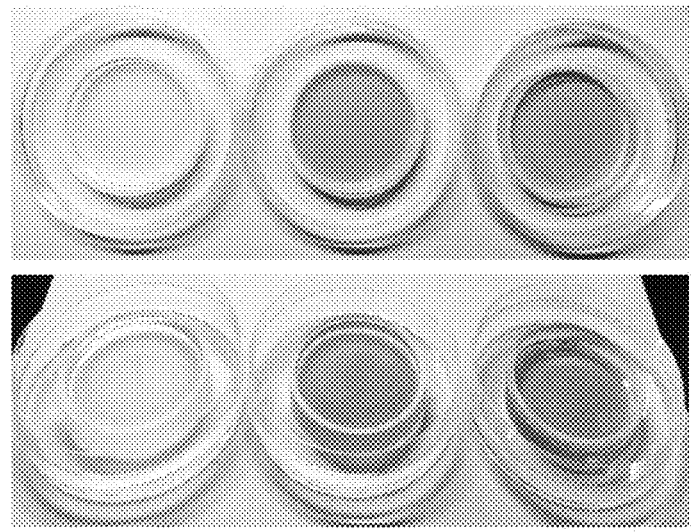
Agarose only    Agarose + PDA    Agarose + PDA (70 °C, heating)

ULTRASOUND PHANTOM FOR FOCUSED ULTRASOUND, METHOD FOR MANUFACTURING THE SAME, BIOMIMETIC HYDROGEL PHANTOM, METHOD FOR MANUFACTURING THE SAME, DISCOLORING METHOD AND DRUG DELIVERING METHOD USING THE SAME

CROSS-REFERENCE TO RELATED APPLICATIONS

This application claims the priority of Korean Patent Application No. 10-2016-0060110 filed on May 17, 2016, in the Korean Intellectual Property Office, the disclosure of which is incorporated herein by reference.

BACKGROUND

Field

The present disclosure relates to an ultrasound phantom for a focused ultrasound and more particularly, to an ultrasound phantom for a focused ultrasound which has a similar speed of sound in a human body to mimic a biological tissue and in which only a specific part heated by ultrasonic irradiation is discolored, a method for manufacturing the same, and a discoloring method of a target part, and a biomimetic hydrogel phantom which is capable of mimicking a biological tissue and discharging a drug stored in a liposome located in a specific part heated by ultrasonic irradiation to deliver the drug, and a manufacturing method and a drug delivering method using the same.

Description of the Related Art

In the field of radiation therapy, an ultrasonography (USG) is a diagnostic technique which provides images of cross-sections of a human body together with a computed tomography (CT) and a magnetic resonance image (MRI) and shares an important part for diagnosing a disease. Specifically, the ultrasonography provides images of cross-sections of the human body in all directions at real time. Therefore, the ultrasonography is an indispensable and important diagnostic technique to diagnose human diseases. The ultrasonography equipment is cheaper and occupies less space than the CT or MRI equipment so that most hospitals use the ultrasonography as diagnostic devices. However, even though the ultrasonography equipment is quantitatively increased, it is difficult to distinguish diseases due to the lowered resolution of the deteriorated equipment in recent years. Therefore, it is required to determine whether the ultrasonography equipment is appropriate as a diagnostic device by periodically evaluating the performance of the ultrasonography equipment using an ultrasonic phantom.

An appropriate scatterer is dispersed in water to be used as the ultrasonic phantom at an earlier stage. However, in this case, various complex problems such as floating matter generated when the water is decayed or layer separation of the scatterer are generated. Therefore, there is a limitation for usage.

Thereafter, an inorganic filler scatterer such as pumice stone or talc is dispersed in a base resin such as a glue or zerdine to manufacture an ultrasound phantom. However, an expiration date for using the ultrasound phantom is very restricted due to dehydration of the base resin or irregular dispersion of the scatterer.

Currently, in the case of a phantom 539-ATS (USA) which is entirely imported and widely used, a life-span thereof is approximately 2 to 5 years due to a lack of durability such as hardening, dehydration, and deviation depending on a temperature caused as time goes by.

Therefore, in order to overcome the above-described problem, studies have been made to use a polymer resin which does not suffer dehydration and alteration or deformation by microorganism as a base and uniformly disperse the scatterer in the polymer resin to extend the available expiration date of the ultrasonic phantom and improve the ultrasound diagnostic performance.

Further, development of a tissue equivalent material which is used for the ultrasound phantom is the foundation for manufacturing not only ultrasound diagnostic phantom, but also various human organs for ultrasound such as breast, thyroid gland, or uterus. Therefore, development of ultrasound phantom for evaluating a performance of the ultrasound diagnostic equipment is very important.

In order to confirm a safety of a patient and clinical effectiveness of an ultrasound heat therapy, it is important to perform a general quality assurance (QA) test checking whether the device generates a thermal lesion. It is difficult to observe a thermal lesion in a visually opaque biological tissue. In order to assure the effectiveness and the safety of the therapy using the ultrasound heat effect, a phantom which visualizes the ultrasound heat effect for a tissue mimicking (TM) thermal lesion which is transparent at a room temperature and has a sound and a heat transfer characteristic similar to the biological tissue is necessary. As existing phantoms which have been developed for this purpose, there are a protein based phantom and an isopropyl acrylamide (NIPA) phantom.

The protein based phantom is used by many researchers to study the heat effect of the ultrasound wave on the biological tissue. This phantom is configured by adding protein (bovine serum albumin or egg white) as a temperature sensitive material in polyacrylamide gel which is visually transparent at a room temperature in order to visualize the thermal lesion which is induced by HIFU. When the HIFU is irradiated onto the phantom, the thermal lesion in which the phantom is converted to be white opaque due to denaturation of the protein is visually observed and the phantom is usefully used to study correlation of the HIFU condition and the thermal lesion.

However, the protein based phantom has lots of disadvantages. First, the denaturation of the protein is irreversible to the temperature. Therefore, once phantom is used, the thermal lesion by the thermal denaturalization permanently remains on the phantom, so that the phantom cannot be reused. Second, a critical temperature (70° C. or lower) at which the protein denaturalization begins is fixed. Therefore, the visualization through the phantom is allowed only under a condition which exceeds this temperature. When a hyperthermia therapy is considered, a temperature which is approximately 40 to 45° C. needs to be maintained by the thermal effect of the ultrasound wave. However, the protein based phantom cannot be used for evaluation.

Third, sound and thermal characteristics of the protein based phantom of the related art are significantly different from those of the biological tissue. For example, an attenuation coefficient of the protein based phantom is much lower than that of the tissue (approximately, 60%) and the ultrasound wave is not scattered, which is different from the tissue. A non-linear parameter (B/A) which is important for a non-linear field such as HIFU is different from that of the tissue.

Fifth, the protein is expensive. Further, when the protein is denaturized, the protein cannot be reused. Therefore, the economic efficiency of the protein is low. For reference, isopropyl acrylamide consumed for manufacturing 50 ml of phantom is approximately 10 dollars.

An isopropyl acrylamide (NIPA) phantom is a transparent tissue which is similar to a gel formed by a mixture of isopropyl acrylamide which is a temperature sensitive polymer and is pending for patent application in the United States (PCT Application No. PCT/CN2009/000161 by Tian Y and Ye F). The isopropyl acrylamide phantom which is transparent at the room temperature is turned into white as the temperature rises. When the heat is removed, the isopropyl acrylamide phantom is turned to be transparent. Therefore, the isopropyl acrylamide phantom is repeatedly used. A temperature at which the transparency is changed may be adjusted in accordance with the selected material or a content of the material within a restricted range. However, the isopropyl acrylamide phantom has the following disadvantages.

First, when an acryl amide component is changed to adjust the temperature range at which the transparency is changed, an acoustic characteristic (for example, an attenuation coefficient of the ultrasound wave) of the phantom is also changed. Therefore, it is difficult to maintain the phantom to be acoustically similar to the tissue. Second, actually, it is not verified whether the acoustic characteristic and the thermal characteristic are similar to those of the biological tissue. It is presented that the speed of sound and the sound impedance of the isopropyl acrylamide phantom are similar to those of the tissue. However, attenuation which is a major acoustic characteristic, dispersion, a nonlinear parameter, and the thermal characteristic have not been evaluated. Third, like the protein BSA, isopropyl acrylamide which is a major component of the phantom is expensive. For example, isopropyl acrylamide consumed for manufacturing 50 ml of phantom is approximately 20 dollars. Fifth, a preparing process of the propyl acrylamide phantom is complex. Further, it takes lots of time (48 hours) to manufacture a single phantom. Furthermore, for preparing nitrogen, a special condition needs to be provided, a special environment needs to be provided and a trained expert is necessary. Therefore, a realizable possibility is low.

RELATED ART DOCUMENT

Patent Document (Patent Document 1) Korean Unexamined Patent Application Publication No. 2008-0080510
(Patent Document 2) Korean Patent Registration No. 1134051
(Patent Document 3) Korean Unexamined Patent Application Publication No. 2014-0001037
(Patent Document 4) Korean Unexamined Patent Application Publication No. 2014-0113173

SUMMARY

The present disclosure has been made in an effort to provide an ultrasound phantom for focused ultrasound which has a speed of sound similar to a speed of sound in a human body and in which when a focused ultrasound is irradiated to heat a specific part, only the specific part is gradually discolored and a method for manufacturing the same.

The present disclosure has been made in an effort to further provide a biomimetic hydrogel phantom which has a speed of sound similar to a speed of sound in a human body and in which when a focused ultrasound is irradiated onto a specific part to heat the specific part, a target material included in a delivery material located in the specific part is discharged and delivered, and a method for manufacturing the same.

Meanwhile, other technical objects to be achieved in the present disclosure are not limited to the aforementioned technical objects, and other not-mentioned technical objects will be obviously understood by those skilled in the art from the description below.

According to a first aspect of the present disclosure, there is provided an ultrasound phantom which mimics a body so as to correspond to a speed of sound in the body. Herein, agarose, sucrose, a temperature sensitive material, and distilled water are mixed and a heated specific part onto which an ultrasound wave is irradiated by a focused ultrasound transducer is gradually discolored in accordance with a temperature.

Further, 3 to 12 wt % of the agarose and 10 to 50 wt % of the sucrose may be included.

Further, the temperature sensitive material may be polydiacetylene vesicle.

Further, the polydiacetylene vesicle may be mixed at a concentration of more than 0 and μM or less.

Further, the polydiacetylene vesicle may be a polymer of a compound represented by the following Formula 1 or a composite polymer induced from a composite of the compound represented by Formula 1 and phospholipid.

[Formula 1]

In Formula 1, $R_1$ is an alkyl group having 3 to 18 carbon atoms, $R_2$ is an alkyl group having 1 to 16 carbon atoms, and $R_3$ is any one selected from the group consisting of an epoxy group, —OH, —COOH, —COH, —NCO, —NCS, —CON$_3$, —OP(O$^{2-}$)OH, or —SH functional groups.

According to a second aspect of the present disclosure, there is provided a method for manufacturing an ultrasound phantom which mimics a body so as to correspond to a speed of sound in the body. The method includes: a first step of melting agarose and sucrose in distilled water; a second step of putting and mixing a mixture in a heated mixing tank; a third step of mixing polydiacetylene vesicle; a fourth step of putting the mixture manufactured in the third step in a heated mold to be cooled and solidified; and a fifth step of removing the mold to separate an ultrasound phantom.

Further, the polydiacetylene vesicle may be manufactured by the steps of manufacturing a stock solution by melting a compound represented by the following Formula 1 and phospholipid in chloroform, respectively; manufacturing a thin film by mixing 0 to 50 mol % of phospholipid in the compound represented by Formula 1 and then removing the chloroform; melting the thin film by putting distilled water; and dispersing the mixture using an ultrasound disperser.

[Formula 1]

In Formula 1, $R_1$ is an alkyl group having 3 to 18 carbon atoms, $R_2$ is an alkyl group having 1 to 16 carbon atoms, and $R_3$ is any one selected from the group consisting of an epoxy group, —OH, —COOH, —COH, —NCO, —NCS, —CON$_3$, —OP(O$^2$)OH, or —SH functional groups.

Further, in the first step, 3 to 12 wt % of agarose and 10 to 50 wt % of sucrose may be mixed and in the third step, the polydiacetylene vesicle may be mixed at a concentration of more than 0 and 100 μM or less.

According to a third aspect of the present disclosure, there is provided method for discoloring a target part using an ultrasound phantom. The method includes the steps of: manufacturing an ultrasound phantom by the manufacturing method according to the second aspect; setting a specific position of the ultrasound phantom to be discolored; irradiating an ultrasound wave onto the ultrasound phantom by controlling a focused ultrasound transducer to focus the specific position through the focused ultrasound transducer; and gradually discoloring the specific position by heating the specific position.

Further, in the step of discoloring, the specific position may be gradually discolored from blue to red.

According to a fourth aspect of the present disclosure, there is provided a biomimetic hydrogel phantom. Herein, agarose, sucrose, a delivery material including a target material, and distilled water may be mixed, and the target material in the delivery material which is located in a specific part onto which an ultrasound wave is irradiated by a focused ultrasound transducer to be heated is discharged.

Further, the delivery material may be polydiacetylene vesicle including a target material.

Further, the target material may be a drug or a fluorescent pigment.

Further, 3 to 12 wt % of the agarose and 10 to 50 wt % of the sucrose may be included and the polydiacetylene vesicle including the target material is mixed at a concentration of more than 0 and 100 μM or less.

Further, the polydiacetylene vesicles a polymer of a compound represented by the following Formula 1 or a composite polymer induced from a composite of the compound represented by Formula 1 and phospholipid.

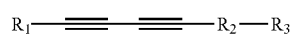
[Formula 1]

In Formula 1, $R_1$ is an alkyl group having 3 to 18 carbon atoms, $R_2$ is an alkyl group having 1 to 16 carbon atoms, and $R_3$ is any one selected from the group consisting of an epoxy group, —OH, —COOH, —COH, —NCO, —NCS, —CON$_3$, —OP(O$^{2-}$)OH, or —SH functional groups.

According to a fifth aspect of the present disclosure, there is provided a method for manufacturing a biomimetic hydrogel phantom. The method includes: a first step of melting agarose and sucrose in distilled water; a second step of putting and mixing a mixture in a heated mixing tank; a third step of mixing polydiacetylene vesicle including a target material; a fourth step of putting the mixture manufactured in the third step in a heated mold to be cooled and solidified; and a fifth step of removing the mold to separate a phantom.

Further, the polydiacetylene vesicle including a target material may be manufactured by the steps of: manufacturing a stock solution by melting a compound represented by the following Formula 1 and phospholipid in chloroform, respectively; manufacturing a thin film by mixing 0 to 50 mol % of phospholipid in the compound represented by Formula 1 and then removing the chloroform; manufacturing a stock solution by melting the target material in distilled water and then adding the stock solution in the film shaped mixture; dispersing the stock solution and the mixture using an ultrasound disperser; removing the remaining target material; and irradiating an ultrasound wave to heat.

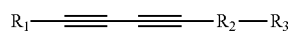
[Formula 1]

In Formula 1, $R_1$ is an alkyl group having 3 to 18 carbon atoms, $R_2$ is an alkyl group having 1 to 16 carbon atoms, and $R_3$ is anyone selected from the group consisting of an epoxy group, —OH, —COOH, —COH, —NCO, —NCS, —CON$_3$, —OP(O$^{2-}$)OH, or —SH functional groups.

According to a sixth aspect of the present disclosure, there is provided a method for delivering a target material in a specific position. The method includes the steps of: manufacturing a phantom by the manufacturing method according to the fifth aspect; setting a specific position of the phantom onto which a target material is discharged; irradiating an ultrasound wave onto the phantom by controlling a focused ultrasound transducer to focus the specific position through the focused ultrasound transducer; and discharging the target material from the polydiacetylene vesicle including a target material including a target material which is located in the specific position.

According to the ultrasound phantom for a focused ultrasound according to the exemplary embodiment of the present disclosure, the ultrasound phantom has a speed of sound which is similar to a speed of sound in the human body. When a focused ultrasound is irradiated onto a specific part to heat the specific part, the specific part is gradually discolored.

The present disclosure has been made in an effort to further provide a biomimetic hydrogel phantom which has a speed of sound similar to a speed of sound in a human body. When a focused ultrasound is irradiated onto a specific part to heat the specific part, a target material included in a delivery material located in the specific part is discharged and delivered.

Meanwhile, the effects to be achieved by the present disclosure are not limited to aforementioned effects and other effects, which are not mentioned above, will be apparently understood by those skilled in the art from the following description.

BRIEF DESCRIPTION OF THE DRAWINGS

The accompanying drawings in the specification illustrate an exemplary embodiment of the present disclosure. The technical spirit of the present disclosure will be more clearly understood from the following detailed description taken in conjunction with the accompanying drawings. Therefore, the present disclosure will not be interpreted to be limited to the drawings:

FIG. 1 is a flowchart of a method for manufacturing an ultrasound phantom for a focused ultrasound according to an exemplary embodiment of the present disclosure;

FIG. 2 is a flowchart of a method for manufacturing a polydiacetylene liposome according to an exemplary embodiment of the present disclosure;

FIG. 3 is a configuration view of an apparatus for discoloring a target part of an ultrasound phantom using a focused ultrasound transducer according to an exemplary embodiment of the present disclosure;

FIG. 4 is a flowchart of a method for discoloring a target part using an ultrasound phantom according to an exemplary embodiment of the present disclosure;

FIG. 5 is a flowchart of a method for manufacturing a biomimetic hydrogel phantom according to an exemplary embodiment of the present disclosure;

FIG. 6 is a flowchart of a method for manufacturing a polydiacetylene liposome including a target material according to an exemplary embodiment of the present disclosure;

FIG. 7 is a flowchart of a method for delivering a target material using a biomimetic hydrogel phantom according to an exemplary embodiment of the present disclosure;

FIGS. 8A and 8B are pictures of a phantom in which 5% of agarose and 0%, 10%, 20%, 30%, 40%, and 50% of sucrose are mixed according to a first exemplary embodiment of the present disclosure;

FIG. 9 is a graph of a speed of sound in accordance with a ratio of sucrose with respect to the phantom illustrated in FIGS. 8A and 8B;

FIGS. 10A and 10B are pictures of phantom in which 10% of agarose and 0%, 10%, 20%, 30%, 40%, and 50% of sucrose are mixed according to a first exemplary embodiment of the present disclosure;

FIG. 11 is a graph of a speed of sound in accordance with a ratio of sucrose with respect to the phantom illustrated in FIGS. 10A and 10B;

FIG. 12 is a table representing a speed of sound in accordance with a ratio of agarose and sucrose;

FIG. 13 is a photograph of a phantom for ultrasound measurement in which a PDA liposome with a concentration of 0 μm, 5 μm, 20 μm, and 50 μm is mixed with 5% of agarose and 30% of sucrose manufactured according to a second exemplary embodiment of the present disclosure;

FIG. 14 is a graph illustrating a speed of sound of the phantom of FIG. 13;

FIG. 15 is pictures of a phantom (left) before adding a PDA liposome and an ultrasound phantom for focused ultrasound manufactured according to a fourth exemplary embodiment of the present disclosure;

FIGS. 16A and 16B are photographs when an ultrasound wave is irradiated on a target part of the ultrasound phantom for focused ultrasound manufactured according to the fourth exemplary embodiment of the present disclosure;

FIG. 17 is a photograph of an ultrasound phantom for focused ultrasound manufactured according to a fourth exemplary embodiment of the present disclosure illustrating color changes at 25° C., 40° C., 50° C., 60° C., and 70° C.;

FIGS. 18 and 19 are schematic diagrams illustrating a manufacturing step of a PDA liposome including a target material manufactured according to a fifth exemplary embodiment of the present disclosure and a method for delivering a target material using a phantom manufactured according to a sixth exemplary embodiment of the present disclosure; and FIG. 20 illustrates pictures of a phantom in which agarose and sucrose are mixed and a phantom in which a PDA liposome including a target material is mixed, and the phantom which is heated at 70° C.

DETAILED DESCRIPTION OF THE EMBODIMENT

The above and other objects, features and other advantages of the present disclosure will be more clearly understood from the following detailed description taken in conjunction with the accompanying drawings. As those skilled in the art would realize, the present disclosure is not limited to the described embodiments, but may be embodied in different ways. On the contrary, exemplary embodiments introduced herein are provided to make disclosed contents thorough and complete and sufficiently transfer the spirit of the present invention to those skilled in the art.

In this specification, when a component is referred to as being "on" another component, it may be directly on the other component, or intervening third component may be present. Further, in the drawings, the thicknesses of components are exaggerated for effectively describing the technical contents.

Exemplary embodiments described in this specification may be described with reference to cross-sectional views and/or plan views which are ideal exemplary views of the present disclosure. Further, in the drawings, the thicknesses of film and regions are exaggerated for effectively describing the technical contents. Therefore, a shape of the exemplary view may be modified by a manufacturing technology and/or an allowable error. Accordingly, exemplary embodiments of the present disclosure are not limited to specific illustrated types but may include modified types which are generated in accordance with the manufacturing process. For example, a region illustrated to have a right angle may be rounded or have a predetermined curvature. Therefore, regions illustrated in the drawings have properties. Shapes of the regions illustrated in the drawings are provided to illustrate a specific shape of a region of an element, but not limit the scope of the present disclosure. Although the terms "first", "second", and the like are used for describing various components, these components are not confined by these terms. These terms are merely used for distinguishing one component from the other components. Exemplary embodiments described herein include complementary embodiments thereof.

The terms used in the present specification are for explaining the embodiments rather than limiting the present invention. Unless particularly stated otherwise in the present specification, a singular form also includes a plural form. The term "comprises" and/or "comprising" used in this specification does not exclude the existence or addition of one or more other components.

When the following specific exemplary embodiments are described, various specific contents are provided for more specific description and understanding of the present disclosure. However, those skilled in the art may understand that the specific exemplary embodiment may be described without using the various specific contents. In some cases, a configuration which is generally known and does not directly relate to the present disclosure will be omitted in order to avoid confusion.

Configuration and Manufacturing Method

Hereinafter, a configuration of an ultrasound phantom for a focused ultrasound according to an exemplary embodiment of the present disclosure and a method for manufacturing the same, and a method for discoloring a target part using the ultrasound phantom will be described.

An ultrasound phantom according to an exemplary embodiment of the present disclosure mimics a body corresponding to a speed of sound in the body and is configured by mixing agarose, sucrose, a temperature sensitive material, and distilled water. In the ultrasound phantom for a focused ultrasound wave, an ultrasound wave is irradiated on a specific part by a focused ultrasound transducer and the heated specific part is gradually discolored in accordance with a temperature.

In an exemplary embodiment of the present invention, 3 to 12 wt % of agarose and 10 to 50 wt % of sucrose are included and the temperature sensitive material is configured by polydiacetylene (PDA) liposome. The polydiacetylene liposome is mixed at a concentration of more than 0 and 100 μM or less.

FIG. 1 illustrates a flowchart of a method for manufacturing an ultrasound phantom for a focused ultrasound according to an exemplary embodiment of the present disclosure. As illustrated in FIG. 1, first, agarose and sucrose are melted in distilled water. 3 to 12 wt % of agarose and 10 to 50 wt % of sucrose are mixed and heated to be melted in distilled water in step S1. Further, the mixture is put in a heated mixing tank to mix the mixture in step S2.

Next, polydiacetylene liposome is mixed with the mixture in step S3. Polyacetylene liposome is mixed at a concentration of more than 0 and 100 μM or less. Further, the manufactured mixture is put in a heated mold to be cooled and solidified in step S4. The mold is removed to separate the ultrasound phantom in step S5.

FIG. 2 illustrates a flowchart of a method for manufacturing a polydiacetylene liposome according to an exemplary embodiment of the present disclosure. According to the method for manufacturing polydiacetylene liposome mixed in step S3, as illustrated in FIG. 2, 10,12-pentacosadiynoic acid and L-α-phosphatidylcholine are melted in chloroform respectively to manufacture stock solution in step S11.

Then, 10,12-pentacosadiynoic acid stock solution and L-α-phosphatidylcholine stock solution are mixed at a ratio of 2.5 to 3.5:0.7 to 1.3 and then chloroform is removed to manufacture a thin film in step S12.

Next, distilled water is put to melt the thin film in step S13 and the mixture is dispersed by an ultrasound disperser in step S14. Further, the mixture is filtered by a cellulose filter and a final compound is stabilized at 1 to 8° C. for 10 to 14 hours and manufactured in step S15.

Hereinafter, a method for discoloring a target part of the ultrasound phantom for a focused ultrasound described above will be described. FIG. 3 illustrates a configuration view of an apparatus for discoloring a target part of an ultrasound phantom using a focused ultrasound transducer according to an exemplary embodiment of the present disclosure. Further, FIG. 4 illustrates a flowchart of a method for discoloring a target part using an ultrasound phantom according to an exemplary embodiment of the present disclosure.

First, the ultrasound phantom for a focused ultrasound is manufactured using the above-mentioned manufacturing method according to the exemplary embodiment of the present disclosure in step S21. Further, as illustrated in FIG. 3, a focused ultrasound transducer which is connected to a signal generator and a power amplifier is provided at a lower part of a water tank and the ultrasound phantom for a focused ultrasound is floated. Further, a specific position of the ultrasound phantom to be discolored is set in step S22.

The focused ultrasound transducer is controlled to focus the set specific position to irradiate an ultrasound wave onto the ultrasound phantom in step S23. When the ultrasound wave is irradiated, the specific position is heated and gradually discolored in step S24. The specific position is gradually discolored from blue to red.

Hereinafter, a configuration and a manufacturing method of a biomimetic hydrogel phantom according to an exemplary embodiment of the present disclosure will be described. The phantom is used to determine and analyze whether to have a speed of sound which is similar to a speed of sound in a human body and to discharge a target material included in a delivery material when an ultrasound wave is irradiated in the human body.

In the biomimetic hydrogel phantom according to the exemplary embodiment of the present disclosure, agarose, sucrose, a delivery material including a target material, and distilled water are mixed and the ultrasound wave is irradiated by the focused ultrasound transducer to discharge a target material in the delivery material which is located in a heated specific part.

The delivery material according to the exemplary embodiment of the present disclosure is configured by polydiacetylene liposome including the target material. Further, the target material may be a drug or a fluorescent material and include 3 to 13 wt % of agarose and 10 to 50 wt % of sucrose. The polydiacetylene liposome including the target material is mixed at a concentration of more than 0 and 100 μM or less.

FIG. 5 illustrates a flowchart of a method for manufacturing a biomimetic hydrogel phantom according to an exemplary embodiment of the present disclosure. Further, FIG. 6 illustrates a flowchart of a method for manufacturing a polydiacetylene liposome including a target material according to an exemplary embodiment of the present disclosure.

First, agarose and sucrose are melted in distilled water in step S31. 3 to 12 wt % of agarose and 10 to 50 wt % of sucrose are melted in distilled water. Further, the mixture is put in a heated mixing tank to mix the mixture in step S32. Next, polydiacetylene liposome including a target material is mixed in step S33.

Further, the manufactured mixture is put in a heated mold to be cooled and solidified in step S34. Next, the mold is removed to separate the phantom in step S35.

According to the method for manufacturing polydiacetylene liposome including a target material to be mixed in step S33, as illustrated in FIG. 6, 10,12-pentacosadiynoic acid and L-α-phosphatidylcholine are melted in chloroform, respectively, to manufacture stock solution in step S41.

Then, 10,12-pentacosadiynoic acid stock solution and L-α-phosphatidylcholine stock solution are mixed at a ratio of 0.5 to 1.5:0.5 to 1.5 and then chloroform is removed to manufacture a thin film in step S42.

Next, the target material is melted in the distilled water to manufacture a stock solution and then the stock solution is added to a thin film in step S43. Next, the mixture is dispersed in an ultrasound disperser in step S44 and the remaining target material is removed in step S45. Further, the ultrasound wave is irradiated to heat the mixture and manufacture the polydiacetylene liposome including a target material in step S46.

FIG. 7 illustrates a flowchart of a method for delivering a target material using a biomimetic hydrogel phantom according to an exemplary embodiment of the present disclosure. As illustrated in FIG. 7, in a method for delivering a target material to a specific position using a biomimetic hydrogel phantom, a biomimetic hydrogel phantom is manufactured by the above-described manufacturing method according to the exemplary embodiment of the present disclosure in step S51.

Further, a specific position of the phantom to which the target material is discharged is set in step S52. Next, a focused ultrasound transducer is controlled to focus the specific position by the focused ultrasound transducer to irradiate an ultrasound wave onto the phantom in step S53.

The target material is discharged from polydiacetylene liposome including the target material located in a specific position in step S54.

EXAMPLES

Hereinafter, specific examples of the present disclosure will be described. First, examples 1 and 3 are examples of manufacturing a mixed phantom for measuring a speed of sound to select a mixture ratio having a speed of sound which is similar to a speed of sound in a human body.

Example 1

To Manufacture Agarose and Sucrose Mixed Phantom for Measuring Speed of Sound In order to manufacture a phantom for measuring a speed of sound in which agarose and sucrose are mixed, 1 g (5%, w/v) of agarose and 6 g (30%, w/v) of sucrose are put in a 100 ml beaker and distilled water is added thereto to make a total volume 20 mL. Next, the mixture is heated in a microwave for two minutes to completely melt the mixture in the distilled water. Next, a melted mixed liquid is poured in a circular acryl cast to be cooled at a room temperature.

By the same manner, phantoms in which 5% of agarose and 0%, 10%, 20%, 40%, and 50% of sucrose are mixed are manufactured, respectively, and phantoms in which 10% agarose and 0%, 10%, 20%, 30%, 40%, and 50% of sucrose are mixed are manufactured, respectively.

FIGS. 8A and 8B illustrate pictures of phantom in which 5% of agarose and 0%, 10%, 20%, 30%, 40%, and 50% of sucrose are mixed according to a first exemplary embodiment of the present disclosure. FIG. 9 illustrates a graph of a speed of sound in accordance with a ratio of sucrose with respect to the phantom illustrated in FIGS. 8A and 8B. As illustrated in FIGS. 8A and 8B, after constantly maintaining a ratio of agarose to be 5%, a ratio of sucrose is changed. In this case, it is understood that as the ratio of the sucrose is increased, the transparency of the phantom is increased. Further, as illustrated in FIG. 9, after constantly maintaining a ratio of agarose to be 5%, a ratio of sucrose is changed. In this case, it is understood that as the ratio of the sucrose is increased, the speed of sound is increased.

FIGS. 10A and 10B illustrate pictures of phantom in which 10% of agarose and 0%, 10%, 20%, 30%, 40%, and 50% of sucrose are mixed according to a first exemplary embodiment of the present disclosure. FIG. 11 is a graph of a speed of sound in accordance with a ratio of sucrose with respect to the phantom illustrated in FIGS. 10A and 10B. As illustrated in FIGS. 10A and 10B, after constantly maintaining a ratio of agarose to be 10%, a ratio of sucrose is changed. In this case, it is understood that as the ratio of the sucrose is increased, the transparency of the phantom is increased. Further, as illustrated in FIG. 11, after constantly maintaining a ratio of agarose to be 10%, a ratio of sucrose is changed. In this case, it is understood that as the ratio of the sucrose is increased, the speed of sound is increased.

FIG. 12 illustrates a table representing a speed of sound in accordance with a ratio of agarose and sucrose. As illustrated in FIG. 12, a speed of sound of a human body is approximately 1540 m/s. Therefore, 5% of agarose and 30% of sucrose which are the close condition to the speed of sound of 1540 m/s are mixed to perform the following examples.

Example 2

To Manufacture PDA Liposome

According to Example 2 of the present disclosure, a PDA liposome which is applied to a phantom is manufactured. 10,12-pentacosadiynoic acid and L-α-phosphatidylcholine are melted in chloroform, respectively, to manufacture 10 mM of stock solution. 10,12-pentacosadiynoic acid stock solution and L-α-phosphatidylcholine stock solution are mixed in a 20 mL vial at a ratio of 3:1 (750 μm:250 μm) and then chloroform is removed using argon gas to manufacture a film shaped mixture.

Further, 10 mL of distilled water is put and then heated at 80° C. for five minutes to melt the film shaped mixture. Next, the mixture is dispersed using a sonicator for 25 minutes. Further, the mixture which is still hot is filtered using 0.4 μm cellulose filter and the filtered final compound is wrapped by a foil and then stabilized at 4° C. for 12 hours to manufacture PDA liposome.

Example 3

To Manufacture Agarose, Sucrose, and PDA Liposome Mixed Phantom for Measuring Speed of Sound For an agarose, sucrose, and PDA liposome mixed phantom, a phantom is manufactured to measure a speed of sound in accordance with a concentration of a PDA liposome.

1 g (5%, w/v) of agarose and 6 g (30%, w/v) of sucrose are put in a 100 ml beaker and distilled water is added thereto to make a total volume 20 mL. Next, the mixture is heated in a microwave for two minutes to completely melt the mixture in the distilled water. 1 mL (50 μM) of FDA liposome manufactured earlier in Example 2 is added at a temperature of 47° C. Further, a mixed liquid in which the PDA liposome is mixed is poured in an acryl circular cast to be cooled at a room temperature to manufacture a phantom.

Similarly, the concentration of the PDA liposome is changed 5 μM, 10 μM, 20 μM, 30 μM, and 40 μM to manufacture phantoms, respectively.

FIG. 13 illustrates a photograph of a phantom for ultrasound measurement in which a PDA liposome with a concentration of 0 μm, 5 μm, 20 μm, and 50 μm is mixed with 5% of agarose and 30% of sucrose manufactured according to a second exemplary embodiment of the present disclosure. As illustrated in FIG. 13, it is understood that as the concentration of the PDA liposome is increased, the phantom is blue. FIG. 14 illustrates a graph illustrating a speed of sound of the phantom of FIG. 13. As illustrated in FIG. 14, it is understood that as the concentration of the PDA liposome is increased, the speed of sound is increased.

Example 4

To Manufacture Ultrasound Phantom for Focused Ultrasound Wave

In Example 4, an ultrasound phantom for a focused ultrasound is manufactured. First, a mold and a mixing tank with a mixer are put in an oven which is maintained at 80° C. Further, 6.5 g (5%, w/v) of agarose and 39 g (30%, w/v) of sucrose are put in a 500 ml beaker and distilled water is added thereto to make a total volume 130 mL.

Further, the mixture is heated by a microwave for five minutes to completely melt the mixture in the distilled water and then the mixing tank and the mold are taken out from the oven. The mixture is poured in the mixing tank to be cooled to a temperature of 60° C.

Further, a lid of the mixing tank is closed and the mixture is mixed using thinky super mixer equipment for two minutes. Next, 6.5 mL (50 μM) of PDA liposome manufactured in Example 2 is added at a temperature of 47° C.

Further, the lid of the mixing tank is closed and the mixture is mixed again using thinky super mixer for two minutes. When the mixing is completed, the mixture is poured carefully so as not to form bubbles in the mold. Further, the lid of the mold is closed and the mold is completely cooled and solidified. Thereafter, the mold is removed to separate the ultrasound phantom for a focused ultrasound wave.

FIG. 15 illustrates pictures of a phantom (left) before adding a PDA liposome and an ultrasound phantom for focused ultrasound manufactured according to a fourth exemplary embodiment of the present disclosure.

FIGS. 16A and 16B illustrate photographs when an ultrasound wave is irradiated on a target part of the ultrasound phantom for focused ultrasound manufactured according to the fourth exemplary embodiment of the present disclosure. As illustrated in FIGS. 16A and 16B, it is understood that when the focused ultrasound with an intensity of 1000 W/cm$^2$ is repeatedly irradiated onto a specific position of the ultrasound phantom using a self-made HIFU device at a frequency of 1.0 MHz for ten seconds, the irradiated specific position is heated and is discolored from blue to red. That is, it is understood that when the high intensity focused ultrasound is irradiated, the temperature of the specific part onto which the ultrasound wave is focused is momentarily increased so that the color of the phantom is changed from blue to red.

Further, FIG. 17 illustrates a photograph of an ultrasound phantom for focused ultrasound manufactured according to the fourth exemplary embodiment of the present disclosure illustrating color changes at 25° C., 40° C., 50° C., 60° C., and 70° C. As illustrated in FIG. 17, it is understood that the ultrasound phantom manufactured according to Example 4 is gradually discolored from blue to red as the temperature rises. When it is determined based on the color change illustrated in FIG. 17, it is estimated that the temperature is increased up to approximately 50° C. by the focused ultrasound wave.

Example 5

To Manufacture PDA Liposome Including Fluorescent Pigment

In Example 5, a FDA liposome including a fluorescent pigment to be mixed in a biomimetic hydrogel phantom is manufactured.

10,12-pentacosadiynoic acid and L-α-phosphatidylcholine are melted in chloroform, respectively, to manufacture 10 mM stock solution. 10,12-pentacosadiynoic acid stock solution and L-α-phosphatidylcholine stock solution are mixed in a 20 mL vial at a ratio of 1:1 (500 m:500 μm) and then chloroform is removed using argon gas to manufacture a film shaped mixture.

Further, Fluorescein which is a fluorescent pigment is melted in the distilled water to manufacture 100 mM stock solution and then 10 mL stock solution is added to the thin film which is manufactured earlier. Next, the mixture is dispersed using a sonicator at 50° C. for 30 minutes. Further, the mixture which is still hot is filtered using a 0.4 μm cellulose filter. Further, the filtered final compound is wrapped by a foil and then stabilized at 4° C. for 12 hours.

Further, the remaining fluorescein pigment is removed using a dialysis (10000 cut off). Finally, 254 nm UV is irradiated on the final compound for three minutes and the final compound is heated at 70° C. for ten minutes to manufacture a PDA liposome including a fluorescent pigment.

Example 6

To Manufacture Biomimetic Hydrogel Phantom

In Example 6, a biomimetic hydrogel phantom is manufactured. First, a mold and a mixer are put in an oven which is maintained at 80° C. Further, 6.5 g (5%, w/v) of agarose and 39 g (30%, w/v) of sucrose are put in a 500 ml beaker and distilled water is added thereto to make a total volume 130 mL.

Further, the mixture is heated by a microwave for five minutes to completely melt the mixture in the distilled water and then the mixing tank and the mold are taken out from the oven. The mixture is poured in the mixing tank to be cooled to a temperature of 60° C.

Further, a lid of the mixing tank is closed and the mixture is mixed using thinky super mixer for two minutes. Next, 6.5 mL (50 μM) of PDA liposome including a fluorescent pigment manufactured in Example 5 is added at a temperature of 47° C.

Further, the lid of the mixing tank is closed and the mixture is mixed again using thinky super mixer for two minutes. When the mixing is completed, the mixture is poured carefully so as not to form bubbles in the mold. Further, the lid of the mold is closed and the mold is completely cooled and solidified. Thereafter, the mold is removed to separate the ultrasound phantom for a focused ultrasound wave.

FIGS. 18 and 19 illustrate schematic diagrams illustrating a manufacturing step of a PDA liposome including a target material manufactured according to a fifth exemplary embodiment of the present disclosure and a method for delivering a target material using a phantom manufactured according to a sixth exemplary embodiment of the present disclosure. FIG. 20 illustrates pictures of a phantom in which agarose and sucrose are mixed and a phantom in which a PDA liposome including a target material is mixed, and the phantom which is heated at 70° C.

As illustrated in FIGS. 18 and 19, it is understood that in Example 5, when 254 nm UV is irradiated, the phantom is blue. When a focused ultrasound is applied to a specific position, the specific position is discolored into red and the fluorescent pigment (target material) included in the PDA liposome is discharged. The PDA liposome discharges a contained target material at approximately 40° C. The PDA liposome is configured by lipid and is in a solid state and a liquid state in accordance with the temperature. That is, at approximately 40° C., the solid-state PDA liposome is turned into a liquid state and thus the contained target material is discharged.

Further, in the apparatus and the method thereof described above, the configuration and method of embodiments as described above may not be applied with limitation, but the embodiments may be configured by selectively combining all or a part of each embodiment such that various modifications may be made.

What is claimed is:

1. An ultrasound phantom for a focused ultrasound wave, which mimics a body so as to correspond to a speed of sound in the body,
   wherein agarose, sucrose, a temperature sensitive material, and distilled water are mixed, a heated specific part onto which an ultrasound wave is irradiated by a focused ultrasound transducer is gradually discolored in accordance with a temperature;
   wherein 3 to 12 wt % of the agarose and 10 to 50 wt % of the sucrose are included;
   wherein the temperature sensitive material is polydiacetylene vesicle;
   wherein the polydiacetylene vesicle is mixed at a concentration of more than 0 and 100 µM or less; and
   wherein the polydiacetylene vesicle is a polymer of a compound represented by the following Formula 1 or a composite polymer induced from a composite of the compound represented by the following Formula 1 and phospholipid:

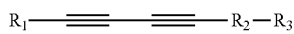

[Formula 1]

In Formula 1, $R_1$ is an alkyl group having 3 to 18 carbon atoms, $R_2$ is an alkyl group having 1 to 16 carbon atoms, and $R_3$ is any one selected from the group consisting of an epoxy group, —OH, —COOH, —COH, —NCO, —NCS, —CON$_3$, —OP(O$^{2-}$)OH, or —SH functional groups.

2. A biomimetic hydrogel phantom,
   wherein agarose, sucrose, a delivery material including a target material, and distilled water are mixed, and
   the target material in the delivery material which is located in a specific part onto which an ultrasound wave is irradiated by a focused ultrasound transducer to be heated is discharged;
   wherein the delivery material is polydiacetylene vesicle including a target material;
   wherein 3 to 12 wt % of the agarose and 10 to 50 wt % of the sucrose are included, and the polydiacetylene vesicle including the target material is mixed at a concentration of more than 0 and 100 µM or less; and
   wherein the polydiacetylene vesicle is a polymer of a compound represented by the following Formula 1 or a composite polymer induced from a composite of the compound represented by the following Formula 1 and phospholipid:

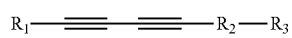

[Formula 1]

In Formula 1, $R_1$ is an alkyl group having 3 to 18 carbon atoms, $R_2$ is an alkyl group having 1 to 16 carbon atoms, and $R_3$ is any one selected from the group consisting of an epoxy group, —OH, —COOH, —COH, —NCO, —NCS, —CON$_3$, —OP(O$^{2-}$)OH, or —SH functional groups.

3. The biomimetic hydrogel phantom according to claim 2, wherein the target material is a drug or a fluorescent pigment.

* * * * *